(12) United States Patent
Thomas et al.

(10) Patent No.: US 7,166,465 B2
(45) Date of Patent: Jan. 23, 2007

(54) CONSTITUTIVE PROMOTER FROM ARABIDOPSIS

(75) Inventors: Terry Thomas, College Station, TX (US); Michael Nuccio, Durham, NC (US); Tzung-Fu Hsieh, Burlingame, CA (US)

(73) Assignee: Rhobio, Lyons Cedex (FR)

( * ) Notice: Subject to any disclaimer, the term of this patent is extended or adjusted under 35 U.S.C. 154(b) by 341 days.

(21) Appl. No.: 10/643,676

(22) Filed: Aug. 19, 2003

(65) Prior Publication Data

US 2005/0176946 A1    Aug. 11, 2005

Related U.S. Application Data

(63) Continuation of application No. PCT/EP02/02894, filed on Feb. 14, 2002.

(60) Provisional application No. 60/270,779, filed on Feb. 22, 2001.

(51) Int. Cl.
*C12N 15/82* (2006.01)
*A01H 5/00* (2006.01)

(52) U.S. Cl. .................. 435/419; 536/24.1; 435/320.1; 800/298; 800/306; 800/312; 800/314; 800/317.2; 800/320; 800/320.1; 800/320.2; 800/320.3; 800/322

(58) Field of Classification Search ............... 536/24.1; 435/320.1, 419; 800/298, 306, 312, 314, 800/317.2, 320, 320.1, 320.2, 320.3, 322
See application file for complete search history.

(56) References Cited

U.S. PATENT DOCUMENTS

| | | | |
|---|---|---|---|
| 4,535,060 A | 8/1985 | Comai | 435/172.3 |
| 4,769,061 A | 9/1988 | Comai | 71/86 |
| 4,810,648 A | 3/1989 | Stalker | 435/191 |
| 4,940,835 A | 7/1990 | Shah et al. | 800/205 |
| 4,971,908 A | 11/1990 | Kishore et al. | 435/172.1 |
| 5,094,945 A | 3/1992 | Comai | 435/172.3 |
| 5,145,783 A | 9/1992 | Kishore et al. | 435/320.1 |
| 5,188,642 A | 2/1993 | Shah et al. | 47/58 |
| 5,310,667 A | 5/1994 | Eichholtz et al. | 435/172.3 |
| 5,312,910 A | 5/1994 | Kishore et al. | 536/23.2 |
| 5,317,096 A | 5/1994 | De Greve et al. | 536/23.71 |
| 5,460,963 A | 10/1995 | Botterman et al. | 435/240.4 |
| 5,530,197 A | 6/1996 | Peferoen et al. | 800/205 |
| 5,545,565 A | 8/1996 | De Greve et al. | 435/320.1 |
| 5,554,798 A | 9/1996 | Lundquist et al. | 800/205 |
| 5,559,024 A | 9/1996 | Leroux et al. | 435/252.3 |
| 5,627,061 A | 5/1997 | Barry et al. | 438/172.3 |
| 5,633,435 A | 5/1997 | Barry et al. | 800/205 |
| 5,633,448 A | 5/1997 | Lebrun et al. | 800/205 |
| 5,635,618 A | 6/1997 | Capellades et al. | 536/24.1 |
| 5,683,691 A | 11/1997 | Peferoen et al. | 424/93.461 |
| 6,037,522 A | 3/2000 | Dong et al. | 800/278 |

FOREIGN PATENT DOCUMENTS

| | | |
|---|---|---|
| EP | 0242236 | 10/1987 |
| EP | 0633317 | 6/1994 |
| WO | 8707644 | 12/1987 |
| WO | 9632488 | 10/1996 |
| WO | 9638567 | 12/1996 |
| WO | 9704103 | 2/1997 |
| WO | 9802562 | 1/1998 |
| WO | 9844781 | 10/1998 |

OTHER PUBLICATIONS

Bevan M. et al. GenBank Accession No. AL022224, Sep. 20, 1999, *Arabidopsis thaliana* DNA chromosome 4, BAC clone F1C12.*
Kim Y.et al. A 20 nucleotide upstream element is essential for the nopaline synthase (nos) promoter activity. Plant Mol Biol. Jan. 1994;24(1):105-17.*
Li Z, Thomas TL. 1998. PEI 1, an Embryo-Specific Zinc Finger Protein Gene Required for Heart-Stage Embryo Formation in *Arabidopsis*. *The Plant Cell* 10:383-398.
Snowden KS, Buchholz WG, Hall TC. 1996. Intron position affects expression from the *tpi* promoter in rice. *Plant Molecular Biology* 31: 689-692.
Thompson JD, Higgins DG, Gibson TJ. 1994. CLUSTAL W: improving the sensitivity of progressive multiple sequence alignment through sequence weighting, position-specific gap penalties and weight matrix choice. *Nucleic Acid Research* 22: 4673-4680.
Bechtold N, Ellis J, Pelletier G. 1993. In planta Agrobacterium mediated gene transfer by infiltration of adult *Arabidopsis thaliana* plants. *Life Sciences* 316:1194-1199.
Morris BAM, Richard KA, Haley A, Zhan X, Thomas JE. 1992. The nucleotide sequence of the infectious cloned DNA component of tobacco yellow dwarf virus reveals features of geminiviruses infecting monocotyledonous plants. *Virology* 187: 633-642.

(Continued)

*Primary Examiner*—Cynthia Collins
(74) *Attorney, Agent, or Firm*—Baker Botts L.L.P.

(57) ABSTRACT

The present invention is directed to a promoter derivable from an *Arabidopsis* ENDO gene. Nucleic acid constructs, vectors, plant cells and transgenic plants comprising the promoter are also provided.

20 Claims, 2 Drawing Sheets

OTHER PUBLICATIONS

Maas C, Laufs J, Grant S, Korfhage C, Werr W. 1991. The combination of a novel stimulatory element in the first exon of the maize Shrunken-1 gene with the following intron 1 enhances reporter gene expression up to 1000-fold. *Plant Molecular Biology* 16:199-207.

Vancanneyt G, Schmidt R, O'Connor-Sanchez A, Willmitzer L, Rocha-Sosa M. 1990. Construction of an intron-containing gene: Splicing of the intron in transgenic plants and its use in monitoring early events in *Agrobacterium*-mediated plant transformation. *Mol. Gen. Genet.* 220: 245-250.

McElroy D, Zhang W, Cao J, Wu R. 1990. Isolation of an efficient actin promoter for use in rice transformation. *The Plant Cell* 2:163-171.

Battraw MJ, Hall TC. 1990. Histochemical analysis of CaMV 35S promoter-β-glucuronidase gene expression in transgenic rice plants. *Plant Molecular Biology* 15:527-538.

Carrington JC, Freed DD. 1990. Cap-independent enhancement of translation by a plant potyvirus 5' nontranslated region. *J. Virology* 64:1590-1597.

Ohta S, Mita S, Hattori T, Nakamura K. 1990. Construction and expression in tobacco of a β-glucuronidase (GUS) reporter gene containing an intron within the coding sequence. *Plant Cell Physiol.* 31:805-813.

Weising K, Schell J, Kahl G. 1988. Foreign genes in plants: transfer, structure, expression, and applications. *Annu. Rev. Genet.* 22:421-477.

Klein TM, Wolf ED, Wu R, Sanford JC. 1987. High-velocity microprojectiles for delivering nucleic acids into living cells. *Nature* 327:70-73.

Callis J, Fromm M, Walbot V. 1987. Introns increase gene expression in cultured maize cells. *Genes & Development* 1:1183-1200.

Jefferson RA, Kavanagh TA, Bevan MW. 1987. GUS fusions: β-glucuronidase as a sensitive and versatile gene fusion marker in higher plants. *EMBO J.* 6:3901-3907.

Bevan M. 1984. Binary Agrobacterium vectors for plant transformation. *Nucleic Acids Research* 12:8711-8721.

Beltz GA, Jacobs KA, Eickbush TH, Cherbas PT, Kafatos FC. 1983. Isolation of multigene families and determination of homologies by filter hybridization methods. *Methods Enzymol.* 100:266-285.

Murphy G, Ridley P, Hudson S, Newes HW, Lemcke K. 2000. Dtabase EMBL Online! Database accession No. AL161552: XP002225702.

* cited by examiner

CONSTITUTIVE PROMOTER FROM *ARABIDOPSIS*

CROSS REFERENCE TO RELATED APPLICATIONS

This application is a continuation of International Patent Application Ser. No. PCT/EP02/02894, filed Feb. 14, 2002, and published in English as WO02/068665 on Sep. 6, 2002, which claims priority to U.S. Provisional Patent Appl. Ser. No. 60/270,779, filed Feb. 22, 2001, the contents of which are incorporated herein in their entireties.

BACKGROUND OF THE INVENTION

The present invention is directed to a promoter derived from an *Arabidopsis* gene. The promoter of the invention is useful in transgenic organisms in which a high level of production of a gene product is desired.

Promoters are regulatory elements that direct the expression of genes. Both constitutive and regulated promoters are used to direct gene expression in transgenic organisms including plants. Constitutive promoters direct expression in most or all tissues, and are useful when high levels of production of a gene product are desired. The 35S promoter from cauliflower mosaic virus (CMV) is frequently used to direct constitutive expression. Regulated promoters, such as tissue-specific and inducible promoters, are used to direct spatially or temporally specific expression, or expression in response to environmental factors.

The present invention is directed to a promoter that directs constitutive expression of genes in plants. The present promoter is derived from a gene of *Arabidopsis* thaliana. In accordance with the present invention, it has been discovered the subject promoter can direct high levels of constitutive expression of heterologous genes in plants.

The present invention is directed to an isolated promoter derived from a gene of *Arabidopsis* thaliana that encodes an endomembrane associated (ENDO) gene. In a preferred embodiment, the promoter has at least 70% identity to the sequence of SEQ ID NO:1. The present invention further provides a nucleic acid construct comprising the promoter of the invention operably linked to a heterologous nucleic acid. Vectors comprising the nucleic acid construct are also provided. In another embodiment, the present invention is directed to a plant cell comprising the nucleic acid construct of the invention. Transgenic plants and progeny thereof comprising the construct, parts of such plants, and methods of making such plants, are also provided.

DETAILED DESCRIPTION OF THE INVENTION

The present invention is directed to a promoter that directs expression of genes in plants.

The promoter is derivable from an *Arabidopsis* gene (ENDO) that encodes an endomembrane-associated protein. In accordance with the present invention, the promoter is derivable from the ENDO gene and is designated the ENDO promoter.

In a preferred embodiment, the ENDO promoter has the sequence of SEQ ID NO:1, or a fragment thereof that has promoter activity, i.e., drives the expression of a heterologous nucleic acid operable linked thereto.

In another preferred embodiment, the ENDO promoter has a sequence that has at least 70% identity to the sequence of SEQ ID NO:1 or a fragment thereof that has promoter activity. More preferably, the ENDO promoter has a sequence that has at least 80%, or more preferably at least 90%, identity to the sequence of SEQ ID NO:1 or a fragment thereof that has promoter activity. Sequence identity as defined herein is measured using the program Clustal W described by Thompson et al. (1994) Nucleic Acid Research 22:4673 and may be calculated using the EMBL Nucleotide Sequence Database.

In another embodiment, the ENDO promoter has a nucleic acid sequence that hybridizes to the sequence of SEQ ID NO:1 under high stringency conditions and that has promoter activity. High stringency conditions are defined herein as 68° C. in buffered aqueous solution or 42° C. in 50% formamide.

The promoters of the present invention may be isolated by using a nucleic acid having the sequence of SEQ ID NO:1 or a fragment thereof to probe a plant genomic library. In a preferred embodiment, the library is an *Arabidopsis* genomic library. Such libraries may be made by well-known methods disclosed for example in Sambrook et al. (1989) Molecular Cloning: A Laboratory Manual, 2nd Edition, Cold Spring Harbor Laboratory Press, Cold Spring Harbor, N.Y. or obtained as a bacterial artificial chromosome (BAC) genomic library from the *Arabidopsis* Biological Resource Center (ABRC) at Ohio State University, 173S Neil Avenue, Columbus, Ohio 43210. The probes can be used to isolate nucleic acids that hybridize to SEQ ID NO:1 under high stringency conditions. High stringency conditions are described in Sambrook et al., id., and Beltz et al. (1983) Methods Enzymol. 100:226 and include, for example, hybridization at 68° C. in aqueous buffered solution or at 42° C. in 50% formamide. Having identified a genomic clone, the promoter can be derived by endonuclease or exonuclease digestion, or PCR amplification.

Further, probes derived from SEQ ID NO:1 may be used to isolate promoters having at least 70%, or at least 80%, or at least 90% identity to SEQ ID NO:1. In addition, well-known methods of enzymatic and chemical synthesis and modification of nucleic acids may be used to obtain promoters having the stated levels of identity to SEQ ID NO:1 or fragments thereof.

The present invention is also directed to methods for isolating a promoter derived from the *Arabidopsis thaliana* ENDO gene comprising (a) probing a plant genome with a nucleic acid having the sequence of SEQ ID NO:1, (b) hybridizing said nucleic acid to a nucleic acid of the plant genome under high stringency conditions, and (c) isolating the promoter from the plant genome. Preferably, the plant genome is an *Arabidopsis* genomic library.

The present invention also encompasses fragments of SEQ ID NO:1 and sequences having at least 70% identity thereto that have promoter activity. Those of ordinary skill in the art can determine the sequence required to maintain promoter activity, for example by generating deletion fragments of SEQ ID NO:1 to obtain putative promoters, operable fusing the putative promoter to a transgene, introducing the construct into a host cell, and measuring expression of the transgene. The transgene may be a reporter, for example, the chloramphenicol acetyl transferase (cat), beta-glucuronidase (gus) or luciferase (luc) genes. The construct containing the promoter and transgene is cloned into a vector, and the vector is used to transform host cells. Expression of the transgene is measured by assaying for the transgene product. Standard assays are available to sensitively detect the reporter gene product. For example, GUS can be measured by histochemical or fluorogenic assays. Jefferson et al.

(1987) EMBO J. 6:3901. The presence of the transgene product is indicative of a functional promoter.

The present invention further provides a nucleic acid construct comprising the promoter operably linked to a heterologous nucleic acid. The heterologous nucleic acid is any nucleic acid other than the ENDO gene. As used herein, the term heterologous nucleic acid includes all synthetically engineered and biologically derived genes which may be introduced into a plant by genetic engineering, including but not limited to nonplant genes, plant genes, modified genes, synthetic genes and portion of genes. The heterologous nucleic acid preferably contains the coding region of a protein or polypeptide or antisense molecule of interest. Suitable heterologous nucleic acids for use herein include all nucleic acids that will provide or enhance a beneficial feature of the resultant transgenic plant. For example, the nucleic acid may encode proteins or antisense RNA transcripts in order to promote increased food values, higher yields, pest resistance, disease resistance, herbicide tolerance, and the like. Representative nucleic acids include, for example, a bacterial dap A gene for increased lysine; genes that encode *Bacillus thuringiensis* (Bt) endotoxins (inter alia U.S. Pat. Nos. 5,460,963; 5,683,691; 5,545,565; 5,530,197; 5,317,096) or insecticidal toxins isolated from *Photorhabdus* (WO97/17432 or WO98/08932) for insect resistance; lytic peptides genes for disease resistance, genes imparting tolerance to oxynil herbicides (U.S. Pat. Nos. 4,810,648 and 5,559,024), bacterial or plant EPSPS for resistance to glyphosate and EPSPS inhibitor herbicides (U.S. Pat. Nos. 4,940,835; 5,188,642; 4,971,908; 5,145,783; 5,312,910; 5,633,435; 5,627,061; 5,310,667, WO 97/04103); genes imparting tolerance to glufosinate (EP 242 236) bacterial or plant HPPD (WO 96/38567, WO 98/02562) for resistance to HPPD-inhibitor herbicides (i.e. diketones, isoxazoles, etc.), chitinase or glucan endo 1,3-B-glucosidase for fungicidal properties. Also, the nucleic acid may be introduced to act as a genetic tool to generate mutants and/or assist in the identification, genetic tagging, or isolation of segments of monocot genes.

As a preferred embodiment of the present invention, the heterologous nucleic acid encodes a protein to impart herbicide tolerance, more preferably tolerance to an oxynil herbicide (disclosed in U.S. Pat. Nos. 4,810,648 and 5,559,024), to EPSPS inhibitor herbicides, including glyphosate and its various salts (disclosed in U.S. Pat. Nos. 4,535,060; 4,769,061; 5,094,945; 4,940,835; 5,188,642; 4,971,908; 5,145,783; 5,312,910; 5,310,667; 5,633,435; 5,627,061; 5,554,798; 5,633,448; WO 97/04103), to glufosinate (EP 242 236), or to HPPD inhibitors (WO 96/38567 and WO 98/02562). More preferably, the heterologous nucleic acid encodes a protein to impart tolerance to EPSPS inhibitor herbicides.

As another preferred embodiment of the present invention, the heterologous nucleic acid 2o encodes a protein to impart insect resistance, more preferably genes which encode for *Bacillus thuringiensis* (Bt) endotoxins (inter alia, U.S. Pat. Nos. 5,460,963; 5,683,691; 5,545,565; 5,530,197; 5,317,096). The nucleic acids that are preferably embraced by the instant invention are cryI, cryII, cryIII, and cryIV genes. More preferably, the genes include: cryIA(a), cryIA(b), cryIA(c); and cryIII(a). Most preferably the gene is cryIA(a), cryIA(b) or cryIA(c). The nucleic acid construct comprising the promoter operably linked to a heterologous nucleic acid may be constructed by methods well-known in the art. The term "operably linked" as used herein means that the promoter and heterologous nucleic acid are oriented such that the promoter directs expression of the heterologous nucleic acid, generally in the 5'- to 3'-direction. The constructs may also contain polyadenylation sites at the 3'-end of the heterologous gene.

In another embodiment, the present invention provides vectors comprising the promoters and nucleic acid constructs of the present invention. The vectors may be derived from plasmids, cosmids, bacteriophage and viruses. The vectors include direct DNA delivery vectors, and vectors for *Agrobacterium*-mediated gene transfer. Direct DNA delivery vectors and *Agrobacterium* based vectors, and methods for their construction, are well-known in the art and disclosed for example in "Gene Transfer to Plants", Potrykus et al., eds., Springer-Verlag, Berlin 1995 and "Plant Molecular Biology: A Practical Approach", Shaw, ed., IRL Press, Oxford 1988.

Vectors for direct DNA delivery generally contain the nucleic acid construct of the invention in a selectable bacterial replicon, and may further contain additional regulatory elements, reporter genes, and selectable markers. Vectors for *Agrobacterium*-mediated gene transfer generally contain functions to allow maintenance in *E. coli* and *Agrobacterium*, transfer from *E. coli* to *Agrobacterium*, and, *Agrobacterium* T-DNA border fragments. The vectors may be integrative or binary vectors. In a preferred embodiment, the vector is a binary vector for *Agrobacterium*-mediated gene transfer.

The vectors may further contain selectable markers and reporter genes to facilitate identification and selection of transformed cells, and suitable regulatory sequences to enable expression in plants. Weising et al. (1988) Annual Rev. Genetics 22:241 describe components that may be included in the subject vectors such as polyadenylation sequences, marker genes, reporter genes, enhancers, and introns.

The present vectors will generally contain either a selectable marker or a reporter gene or both to facilitate identification and selection of transformed cells. Alternatively, the selectable marker may be carried on a separate vector and used in a co-transformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al., supra. A preferred selectable marker gene is the hygromycin B phosphotransferase (hpt) coding sequence, which may be derived from *E. coli*. Other selectable markers known in the art include aminoglyvoside phosphotransferase gene of transposon Tn5 (AphII) which encodes resistance to the antibiotics kanamycin, neomycin, and G418, as well as those genes which code for resistance or tolerance to glyphosate, bialaphos, methotrexate, imidazolinones, sulfonylureas, bromoxynil, dalapon, and the like. Selectable marker genes that confer herbicide tolerance are also of commercial utility in the resulting transformed plants.

To determine whether a particular combination of heterologous nucleic acid and recipient plant cells are suitable for use herein, the vector may include a reporter gene. Reporter genes which encode easily assayable marker proteins are well known in the art. In general, a reporter gene is a gene which is not present or expressed by the recipient organism or tissue and which encodes a protein whose expression is manifested by some easily detectable property, e.g., phenotypic change of enzymatic activity. Examples of such genes are provided in Weising et al., supra. Preferred genes include the chloramphenicol acetyl transferase (cat) gene from Tn9 of *E. coli*, the beta-gluronidase (gus) gene of the uidA locus of *E. coli*, the green fluorescence protein (GFP) gene from *Aequoria victoria*, and the luciferase (luc) gene from the firefly *Photinus pyralis*. An assay for expression of the reporter gene may be performed at a suitable time after the heterologous nucleic acid has been introduced into the recipient cells. A preferred such assay entails the use of the *E. coli* beta-glucuronidase (gus) gene described by Jefferson et al. (1987) EMBO J. 6:3901, incorporated herein by reference. Other elements such as introns, enhancers, polyadenylation sequences and the like, may also be present in the nucleic acid. These elements must be compatible with the remainder of the gene constructions. Such elements may or may not be necessary for the function of the gene, although they may provide a better expression or functioning of the gene by effecting transcription, stability of the mRNA, or the like. Such elements may be included in the nucleic acid as desired to obtain the optimal performance of the transforming gene in the plant. For example, the maize AdhI S first intron may be placed between the promoter and the coding sequence of a particular heterologous nucleic acid. This intron, when included in a gene construction, is known to generally increase expression in maize cells of a protein. (Callis et al. (1987) Genes Dev. 1:1183). Other suitable introns include the first intron of the shrunken-1 gene of maize (Maas et al. (1991) Plant Mol. Biol. 16:199); the first intron of the castor bean catalase (cat-1) gene (Ohta et al. (1990) Plant Cell Physiol. 31:805); potato catalase second intron of the ST-LSI gene (Vancanneyt et al. (1990) Mol. Gen. Genet. 220:245); tobacco yellow dwarf virus DSV intron (Morris et al. (1992) Virology 187:633; actin-1 (act-1) intron from rice (McElroy et al. (1990) Plant Cell 2:163); and triose phosphate isomerase (TPI) intron 1 (Snowden et al. (1996) Plant Mol. Biol. 31:689). However, sufficient expression for a selectable marker to perform satisfactorily can often be obtained without an intron. (Battraw et al. (1990) Plant Mol. Biol. 15:527).

Transcription activators such as enhancers include the tobacco mosaic virus (TMV) translation activator (WO87/07644) and the tobacco etch virus (TEV) translation activator (Carrington et al. (1990) J. Virol. 64:1590). Polyadenylation and terminator regulation sequences include sequences of bacterial origin, such as the nopaline synthase (nos) terminator of *Agrobacterium tumifaciens*, or of plant origin such as the histone terminator (EP 0633317). The vector comprising the heterologous nucleic acid may also comprise sequences coding for a transit peptide, to drive the protein coded by the heterologous gene into the chromoplasts of the plant cells. Such transit peptides are well known to those of ordinary skill in the art, and may include single transit peptides, as well as multiple transit peptides obtained by the combination of sequences coding for at least two transit peptides. One preferred transit peptide is the Optimized Transit Peptide disclosed in U.S. Pat. No. 5,635,618, comprising in the direction of transcription a first DNA sequence encoding a first chloroplast transit peptide, a second DNA sequence encoding an N-terminal domain of a mature protein naturally driven into the chromoplasts, and a third DNA sequence encoding a second chloroplast transit peptide. The constructs of the present invention are introduced into plant cells by methods known in the art. Direct gene transfer methods include gene transfer to protoplasts by microinjection, electroporation, chemically-induced DNA uptake (Potrykus, supra) and biolistic (microprojectible bombardment) approaches (Klein et al. (1987) Nature 327:70). *Agrobacterium* mediated gene transfer methods include leaf disk transformation, protoplast culture, transformation of seed, stem or root explants, in planta vacuum-infiltration (Potrykus, supra), and transformation of inflorescence (U.S. Pat. No. 6,037,522).

Plant cells into which the nucleic acids of the present invention include cells of all plants into which nucleic acids can be transferred. Plant cells include undifferentiated tissues such as calli and differentiated tissues such as embryos, plant portions, plants and seeds. Monocotyledous and dicotyledonous plants are included. In a preferred embodiment the plant is cotton, rice, corn, wheat, barley, oat, rye, oil seed rape, potato, soybean, sunflower, sugar cane, sugar beet, alfalfa, or banana. In a more preferred embodiment, the plant is cotton, corn, or potato, and most preferably cotton.

The promoters, nucleic acid constructs, vectors, and plant cells of the present invention are useful for making recombinant gene products in vitro, and for making transgenic plants with desirable properties.

Another aspect of the invention provides transgenic plants, progeny thereof, and seeds and other parts thereof containing the nucleic acid construct of the present invention. Both monotyledous and dicotyledonous plants are contemplated. Plant cells are transformed with the nucleic acid construct by any of the plant transformation methods described above, and regenerated into a complete transgenic plant by methods well known to those of ordinary skill in the art (Potrykus, supra, Shaw, supra). For in planta transformation methods, the regeneration step is not needed. Generally, germinating seeds or wounded plants are inoculated with *Agrobacterium* containing the nucleic acid construct, plants are grown to maturity, and seeds are collected, sown, and transformants are selected.

A method of making a transgenic plant comprising the nucleic acid construct of the present invention comprises transforming a plant cell with a vector comprising the ENDO promoter operably linked to a heterologous gene to provide a transformed plant cell, and regenerating a transgenic plant from the transformed plant cell. Another method of making a transgenic plant comprising the nucleic acid construct of the present invention comprises transforming a seed or immature plant with a vector comprising the ENDO promoter operably linked to a heterologous gene, growing the seed or plant to maturity, obtaining the seeds of the plant, and generating transgenic plants from the seeds. The transgenic plants of the present invention are useful in that they may express a gene product for a desired property such as insect resistance, pesticide resistance, heat, cold or drought tolerance, herbicide tolerance, improved properties, and so on.

EXAMPLES

Example 1

An *Arabidopsis* root cDNA library was constructed using the lambda ZAPII cDNA library construction kit (Stratagene, La Jolla, Calif.). The cDNA library was converted into plasmid library by mass excision, and bacterial clones were ordered into 384-well microtiter plates. Replica filters were made by gridding four 384-well plates onto a 12 cm×8 cm nylon filter using a Biomek 2000 robot. The filter has a 3×3 grid in each well location. As a result, 1,536 cDNA clones were represented on each nylon filter with each clone having its unique duplicate pattern to eliminate false hybridization signals.

Each replica filter was then hybridized with cDNA probes prepared from various *Arabidopsis* tissues or organs. The random-primed PCR technique (RP-PCR) described by Li et al. (1998) Plant Cell 10:383 was used for cDNA probe preparation to increase the detection sensitivity. Four filters were constructed to represent 6,144 anonymous cDNA clones. Seven filter sets were made and hybridized to RP-PCR probes synthesized from *Arabidopsis* root, leaf, stem, whole silique, silique without seeds, seedling, and flower tissues. The hybridization of each colony to each probe was recorded in a Microsoft Excel database. Sorting algorithms were then utilized to determine the colonies representing putative tissue-specific or constitutive genes. Thirty-three putative constitutive clones were identified and subjected to further characterization. The identity of each clone was determined by DNA sequencing and database searches. RNA dot blot analysis was used to assess the expression pattern of each candidate gene. In order to gain quantitative information on each clone's expression level, RNA dot blot analysis was performed using RNAs isolated from a transgenic *Arabidopsis* line that harbors a 35S:GUS construct (obtained from the *Arabidopsis* Biological Resource Center (ABRC) at Ohio State University, 1735 Neil Avenue, Columbus, Ohio 43210). Relative transcription activity of each gene was then directly compared with the 35S promoter by incorporating a GUS probe in RNA dot blot analysis.

Figure 1:
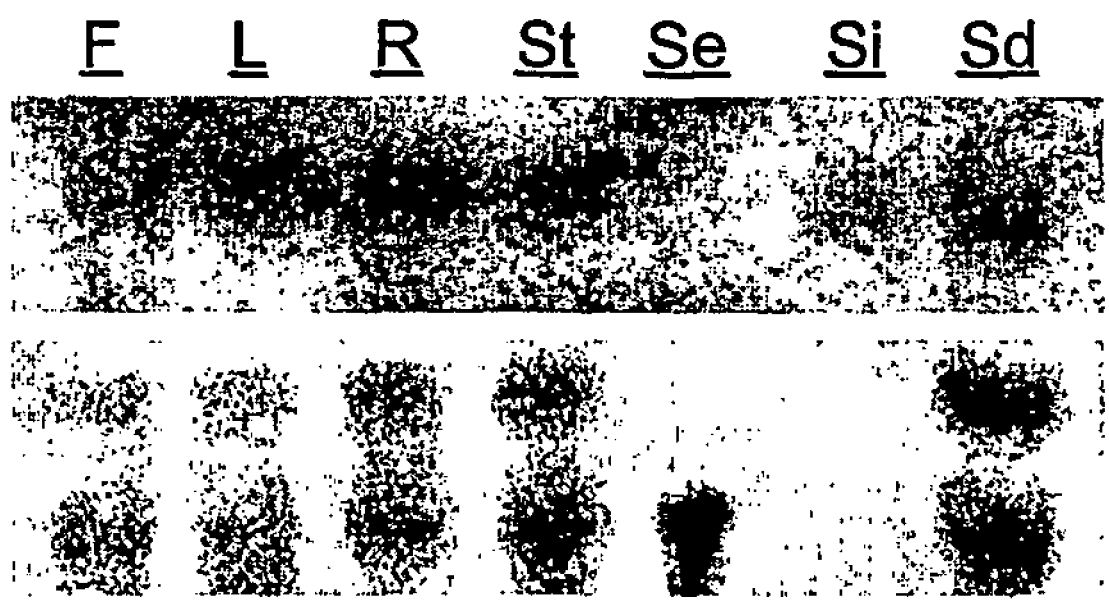
FIG. 1 depicts an RNA gel blot analysis of RC 15 gene expression. Five micrograms of total RNA isolated from stem (St), leaf (L), flower (F), root (R), silique without seed (Si), silique with seeds (Sc) and seedling (Sd) were used to make the RNA gel blot.

A clone designated RC 5 was among the putative constitutive clones chosen for further characterization based on its high levels of expression revealed by RNA dot blot analysis. RNA gel blot analysis showed that CT2 is expressed in most of the tissues examined (stem, leaf, flower, root, silique without seeds, whole silique and seeding) at high levels. (FIG. 1). Sequence analysis indicated that RC15 encoded a putative endomembrane-associated protein. Specifically, a BLASTN search against the GenBank database found that RC15 has been fully sequenced by the EU *Arabidopsis* sequencing project. The BAC clone that contains RC15 is designated F1C12 and was deposited in GenBank as Accession number AL022224 by the EU *Arabidopsis* sequencing project. A portion of F1C12 encodes an endomembrane-associated protein.

F1C12 was retrieved from GenBank, and the location of the putative RC15 promoter region was identified. Two primers were designed to amplify the putative promoter region (corresponding to bases 69721–71740 of F1C12) upstream of the putative translation start site of RC15. The amplified 2 kb promoter fragment is shown as SEQ ID NO:2. SEQ ID NO:2 depicts the amplified product and contains artificial restriction sites (HindIII site at the 5'-end and BamHI site at the 3'-end) introduced during PCR to facilitate cloning. The amplified promoter was isolated and cloned upstream of the plant reporter gene GUS by replacing the 35S promoter of the plant transformation vector pBI121 (Bevan (1984) Nucleic Acids Res. 12:8711) with the amplified promoter. The resulting construct is designated pENDO: GUS.

Example 2

The plasmid pENDO::GUS described in Example 1 was used to transform wild type *Arabidopsis* via vacuum filtration as described by Bechtold et al. (1993) Life Sciences 316:1194. Transgenic plants were recovered and assayed for GUS expression according to Jefferson et al. (1987) EMBO J. 6:3901. Histochemical GUS staining analysis showed that the ENDO promoter drives GUS expression in most of the transgenic plant tissues.

GUS gene expression was found constitutively in all of the major plant tissues. Further, the ENDO promoter drives GUS gene expression throughout the plant life cycle. Thus the ENDO promoter is a constitutive promoter that drives transgene expression in all of the major plant tissues.

Example 3

Figure 2:
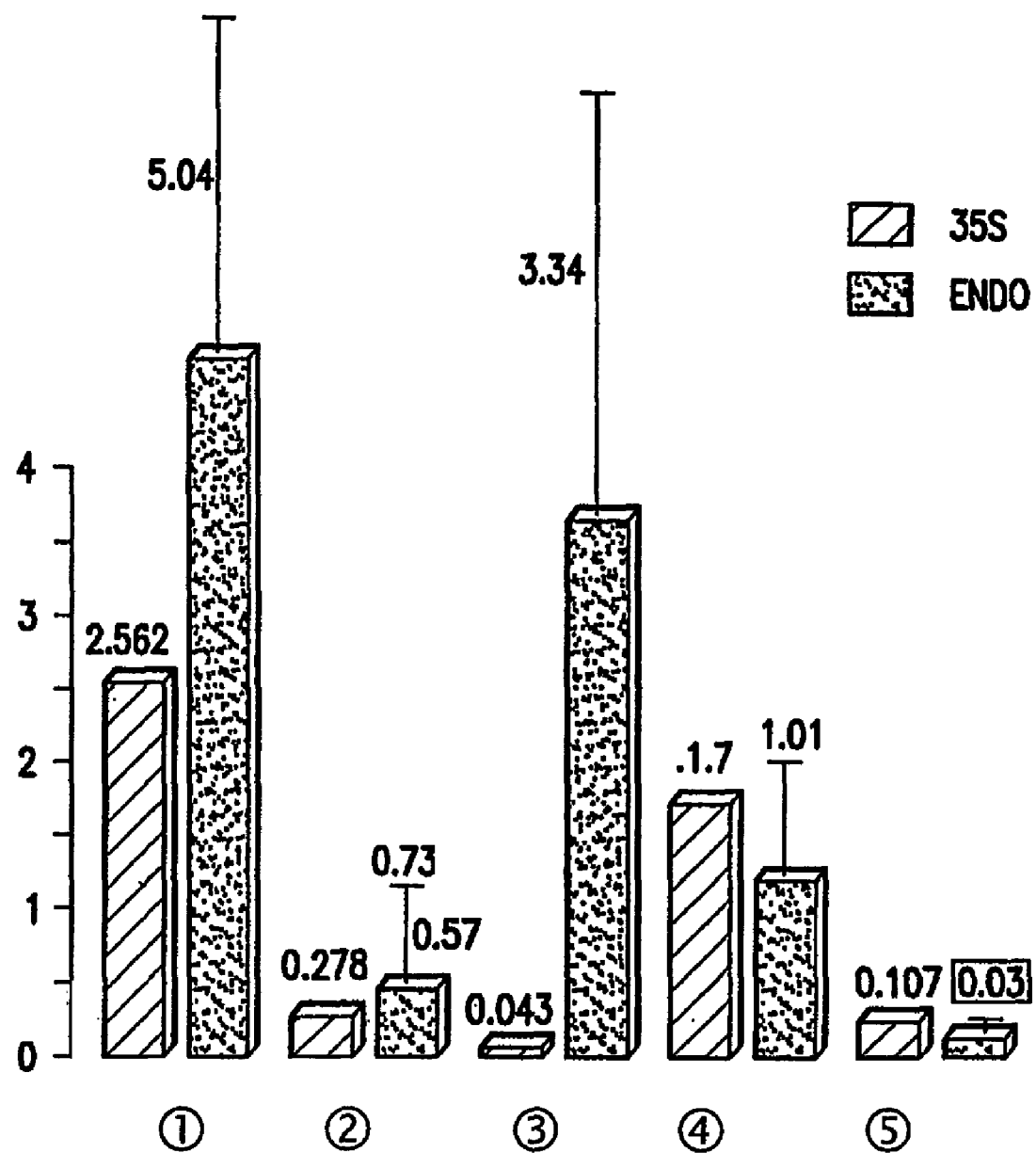
FIG. 2 is a graph comparing relative promoter activity of the 35S and ENDO promoters, as determined by fluorometric beta-glucuronidase (GUS) assays. Light bars represent GUS activity driven by the ENDO promoter. Dark bars represent GUS activities driven by the 35S promoter. Expression was determined in 1 (rosette), 2 (flower), 3 (stem), 4 (silique), and (30 mature seed).

A fluorometric GUS assay was performed to determine the ENDO promoter activity quantitatively according to Jefferson et al., id. Six to eight independent lines were assayed for ENDO promoter activity. FIG. 2 is a graph showing a comparison of relative promoter activity between the 35S and ENDO promoters by fluorometric GUS assays. In FIG. 2, standard deviations are shown above the bars corresponding to activity driven by the ENDO promoter. The y-axis indicates the GUS activity in pmole/mg/min.

As shown in FIG. 2, the activity of the ENDO promoter is comparable to or greater than the 35S promoter. In developing seed, GUS gene expression is relatively low compared to the 35S promoter. Thus the CT2 promoter is ideal for applications in which strong constitutive expression of a transgene is desired in plant tissues except seed. One example is the expression of pesticide resistance genes or insecticidal genes for crop protection, in which expression of such genes in seeds is not desirable.

The invention claimed is:

1. An isolated nucleic acid having the sequence of SEQ ID NO:1 operably linked to a heterologous nucleic acid.

2. A nucleic acid construct comprising an isolated nucleic acid having promoter activity according to claim 1 further comprising a polyadenylation site at the 3' end of the heterologous nucleic acid.

3. A vector comprising an isolated nucleic acid according to claim 1.

4. A plant cell comprising a nucleic acid construct according to claim 2.

5. A transgenic plant or the progeny thereof comprising a nucleic acid construct according to claim 2.

6. The transgenic plant of claim 5 wherein the plant is selected from the group consisting of a monocotyledonous plant and a dicotyledonous plant.

7. The transgenic plant of claim 6 wherein the plant is a plant selected from the group consisting of cotton, rice, corn, wheat, barley, oat, rye, oil seed rape, potato, soybean, sunflower, sugar cane, sugar beet, alfalfa and banana.

8. A vector comprising the nucleic acid construct of claim 2.

9. A plant cell comprising the nucleic acid construct of claim 2.

10. A transgenic plant or the progeny thereof comprising the nucleic acid construct of claim 2.

11. A transgenic plant or the progeny thereof comprising the plant cell of claim 4.

12. A transgenic plant or the progeny thereof comprising the plant cell of claim 9.

13. The transgenic plant of claim 10, wherein the plant is selected from the group consisting of a monocotyledonous plant and a dicotyledonous plant.

14. The transgenic plant of claim 13, wherein the plant is a plant selected from the group consisting of cotton, rice, corn, wheat, barley, oat, rye, oil seed rape, potato, soybean, sunflower, sugar cane, sugar beet, alfalfa and banana.

15. The transgenic plant of claim 11, wherein the plant is selected from the group consisting of a monocotyledonous plant and a dicotyledonous plant.

16. The transgenic plant of claim 15, wherein the plant is a plant selected from the group consisting of cotton, rice, corn, wheat, barley, oat, rye, oil seed rape, potato, soybean, sunflower, sugar cane, sugar beet, alfalfa and banana.

17. The transgenic plant of claim 12, wherein the plant is selected from the group consisting of a monocotyledonous plant and a dicotyledonous plant.

18. The transgenic plant of claim 17, wherein the plant is a plant selected from the group consisting of cotton, rice, corn, wheat, barley, oat, rye, oil seed rape, potato, soybean, sunflower, sugar cane, sugar beet, alfalfa and banana.

19. A vector comprising an isolated nucleic acid according to claim 1 further comprising a polyadenylation site at the 3' end of the heterologous nucleic acid.

20. A transgenic plant or the progeny thereof comprising a plant cell according to claim 4.

* * * * *

SEQUENCE LISTING

```
<160> NUMBER OF SEQ ID NOS: 2

<210> SEQ ID NO 1
<211> LENGTH: 2030
<212> TYPE: DNA
<213> ORGANISM: Arabidopsis thaliana
```

<400> SEQUENCE: 1

```
cttcatagaa ggatggacca ttgaagaata ctttctcttt tctattttta tttgatttag      60
aaaatcatat tcattacaaa aggaaaaaaa aataattttt ttgtatccta aagttataac     120
ttacaatttt ccacacttca gtttggtagt attaatttat ctattttat caaagtttgg     180
ttttaggaaa aatgtatctt ttcatataaa aaatatatag atcttcaaag aaactgaatt     240
gggttttcaa ctattttatc gtttgacact actttgactt atcaaaaaga gttcaaaata     300
gaaaaataga atcgaatcac acgtttcagt gtaagaggga tttgatattg gtcgacattt     360
taaagagttg ttttgttttt ttttccaatc tgcatggttt ttcgttccgt tgaaccaaat     420
tcaacacttt gtataaaccg aatagtaata tactagacgt acgccaatac caaaaataaa     480
attaaaactc aattcacaaa ttgaatctac accatatcat gcatatatat cagcaaccta     540
gaataatcaa tgaaatttaa tcgaggataa tcaatatcca actcaacgat aatcaaaagc     600
ctaataatag atcaatgaaa tcaaataact aaacatagta atatacattg atttgtgtta     660
aacagaataa tatacattat aatagtatga aaatatgaat ataatgagat aagaggcgta     720
tatgttacaa ctacagatca ccatccacaa ttaacaatcc gattggtgcg ggccattgtt     780
tcgatatttg ccaactgtga ttgatgtgac tgccagctgg catattttcc cctcctgatt     840
acgttttac cctttcctct tctgtttcac cgttaattca attttactat ttgtaccgct     900
gtctttcacc ttttttaaga aacccaacc cgaaatcata actataccga aatcacatgt     960
cttcatggtg acgtaacaag acttattttc cggtttgaatt tggtttaacc tattgagatt    1020
gtgctaaccg aaaacagaaa cggttatgac gccaacgagg caagaggggt aaaacgagaa    1080
agaggggatg gcagaaatcg taattaacaa ggaaaataaa gggtggtttc acgataagtc    1140
tgtctatatg acgcgaaagg gtttcttaaa ttcagagaga caattaatca gtttcgtgtg    1200
tttggagaag aagaagaaca gatcaaatac gaggagagat ctctaaagag atttatcgtt    1260
tcaagtaagt ctctttatca aactcttaat ataaacaaat caaaacatga acacgtcgtg    1320
tcttcgtttc gattctagat acgattttt agttcatgtg aatgaactct gttttattac    1380
tactagggtt gttcaatatt tttccgagaa ttaccagagg aacaaagtta gtgattatat    1440
tgatgcagag tatgaagtaa ttatatacat aaatcatgtt ttgttctcaa gcatctacgt    1500
tgaaatatat ataagaagtt ttttttttggt gaaaaaatat gtatgagaag ttcatcttttc    1560
ataatagtga aacaactctc tttcatacca aaaaaaaaat ttgaaaaaaa attagtgaaa    1620
ctctctttgt ccgattaggt taggtttgga ctcagaatca aaatacgatt agcataacaa    1680
attttttggc atggcaatta ttgtctgcag gtaaaatata ccaatagaaa catatttta    1740
ggagtagtta agattatgat tgaagaaata ctattacgat aagcataaaa ttttcttttg    1800
ctgttcttgg tttttgtcgt tttatagaac attgaatatg tacttttgtt ttttttcacc    1860
agtagatatg tactatacac acataagtaa catgggtagt ttatatagag agagatttga    1920
ttttcgtat atttctttttg ttgaaaataa atatgtgtaa aatttattgt ttattaattt    1980
gacagatttg ttcacgttga gaagtttaat ttagattaaa caacaaaaag                2030
```

<210> SEQ ID NO 2
<211> LENGTH: 2042
<212> TYPE: DNA
<213> ORGANISM: Arabidopsis thaliana

<400> SEQUENCE: 2

```
aagcttcttc atagaaggat ggaccattga agaatacttt ctcttttcta tttttatttg      60
```

-continued

```
atttagaaaa tcatattcat tacaaaagga aaaaaaaaat aattttttgt atcctaaagt     120
tataacttac aattttccac acttcagttt ggtagtatta atttatctat ttttatcaaa     180
gtttggtttt aggaaaaatg tatcttttca tataaaaaat atatagatct tcaaagaaac     240
tgaattgggt tttcaactat tttatcgttt gacactactt tgacttatca aaaagagttc     300
aaaatagaaa aatagaatcg aatcacacgt ttcagtgtaa gagggatttg atattggtcg     360
acattttaaa gagttgtttt gttttttttt ccaatctgca tggttttttcg ttccgttgaa     420
ccaaattcaa cactttgtat aaaccgaata gtaatatact agacgtacgc caataccaaa     480
aataaaatta aaactcaatt cacaaattga atctacacca tatcatgcat atatatcagc     540
aacctagaat aatcaatgaa atttaatcga ggataatcaa tatccaactc aacgataatc     600
aaaagcctaa taatagatca atgaaatcaa ataactaaac atagtaatat acattgattt     660
gtgttaaaca gaataatata cattataata gtatgaaaat atgaatataa tgagataaga     720
ggcgtatatg ttacaactac agatcaccat ccacaattaa caatccgatt ggtgcgggcc     780
attgtttcga tatttgccaa ctgtgattga tgtgactgcc agctggcata ttttccctc     840
ctgattacgt ttttacccctt tcctcttctg tttcaccgtt aattcaattt tactatttgt     900
accgctgtct ttcaccttttt ttaagaaaac ccaacccgaa atcataacta taccgaaatc     960
acatgtcttc atggtgacgt aacaagactt attttccggt tgaatttggt ttaacctatt    1020
gagattgtgc taaccgaaaa cagaaacggt tatgacgcca acgaggcaag aggggtaaaa    1080
cgagaaagag gggatggcag aaatcgtaat taacaaggaa aataaagggt ggtttcacga    1140
taagtctgtc tatatgacgc gaagggtttt cttaaattca gagagacaat taatcagttt    1200
cgtgtgtttg gagaagaaga agaacagatc aaatacgagg agagatctct aaagagattt    1260
atcgtttcaa gtaagtctct ttatcaaact cttaatataa acaaatcaaa acatgaacac    1320
gtcgtgtctt cgtttcgatt ctagatacga ttttttagtt catgtgaatg aactctgttt    1380
tattactact agggttgttc aatattttc cgagaattac cagaggaaca aagttagtga    1440
ttatattgat gcagagtatg aagtaattat atacataaat catgttttgt tctcaagcat    1500
ctacgttgaa atatatataa gaagtttttt tttggtgaaa aaatatgtat gagaagttca    1560
tctttcataa tagtgaaaca actctctttc ataccaaaaa aaaaatttga aaaaaaatta    1620
gtgaaactct cttttgtccga ttaggttagg tttggactca gaatcaaaat acgattagca    1680
taacaaattt tttggcatgg caattattgt ctgcaggtaa aatataccaa tagaaacata    1740
tttttaggag tagttaagat tatgattgaa gaaatactat tacgataagc ataaaatttt    1800
cttttgctgt tcttggtttt tgtcgttta tagaacattg aatatgtact tttgttttt    1860
ttcaccagta gatatgtact atacacacat aagtaacatg ggtagtttat atagagagag    1920
atttgatttt tcgtatattt cttttgttga aaataaatat gtgtaaaatt tattgtttat    1980
taatttgaca gatttgttca cgttgagaag tttaatttag attaaacaac aaaaagggat    2040
cc                                                                   2042
```